US009717238B2

(12) United States Patent
Lacerda et al.

(10) Patent No.: US 9,717,238 B2
(45) Date of Patent: Aug. 1, 2017

(54) ANTIBACTERIAL COMPOSITION, ANTIBACTERIAL CASES AND ACCESSORIES FOR HANDHELD ELECTRONICS, AND METHOD OF MAKING ANTIBACTERIAL CASES FOR HANDHELD ELECTRONICS

(71) Applicants: Carlos M. Lacerda, Miami, FL (US); Jorge Metzger, Araricá (BR)

(72) Inventors: Carlos M. Lacerda, Miami, FL (US); Jorge Metzger, Araricá (BR)

( * ) Notice: Subject to any disclaimer, the term of this patent is extended or adjusted under 35 U.S.C. 154(b) by 0 days.

(21) Appl. No.: 14/715,545

(22) Filed: May 18, 2015

(65) Prior Publication Data

US 2015/0327541 A1 Nov. 19, 2015

Related U.S. Application Data

(60) Provisional application No. 61/994,931, filed on May 18, 2014.

(51) Int. Cl.
| | | |
|---|---|---|
| *A61K 9/14* | (2006.01) | |
| *A01N 25/10* | (2006.01) | |
| *A44B 1/02* | (2006.01) | |
| *A44B 1/20* | (2006.01) | |
| *A01N 59/16* | (2006.01) | |

(52) U.S. Cl.
CPC ............ *A01N 25/10* (2013.01); *A01N 59/16* (2013.01); *A44B 1/02* (2013.01); *A44B 1/20* (2013.01); *Y10T 16/458* (2015.01); *Y10T 24/3689* (2015.01)

(58) Field of Classification Search
None
See application file for complete search history.

(56) References Cited

U.S. PATENT DOCUMENTS

| | | | | |
|---|---|---|---|---|
| 2005/0008861 | A1* | 1/2005 | Yadav | C08K 3/08 428/403 |
| 2005/0022328 | A1* | 2/2005 | Weihrauch | A46D 1/00 15/207.2 |
| 2012/0024712 | A1 | 2/2012 | Neumann et al. | |
| 2013/0108678 | A1* | 5/2013 | Santra | A01N 59/16 424/409 |
| 2013/0252021 | A1 | 9/2013 | Neumann et al. | |
| 2013/0302640 | A1 | 11/2013 | Neumann et al. | |
| 2015/0290280 | A1* | 10/2015 | Petrak | A61L 15/44 604/151 |

OTHER PUBLICATIONS

Silver Nano Health System, Silver Nano, Wikipedia (May 28, 2014), https://en.wikipedia.org/wiki/Silver_Nano.
Marcia R. De Moura et al., Development of cellulose-based bactericidal nanocomposites containing silver nanoparticles and their use as active food packaging, journal, (Nov. 7, 2011), vol. 109, Issue 3, p. 520-524, Elsevier, available at http://www.sciencedirect.com/science/article/pii/S0260877411005802.
Alasept, Antibacterial Surface for Fittings, Hafele (May 16, 2014), http://www.hafele.com.cn/cn/en/products/28056.asp.
Conselho Nacional De Desenvolvimento E Tecnologico—CNPQ, RHAE Pesquisador na Empresa, catalog, (2013), p. 39, Brazil, available at http://rhae.cnpq.br/wp-content/uploads/2013/12/catalogo-de-projetos-do-75-2010.pdf.
TNS Nanotechnologia, Antimicrobial (Jul. 15, 2015), http://tnsolution.com.br/en/antimicrobial/.
US Environmental Protection Agency, Notice of Pesticide Registration 84610-2, Issued May 15, 2015.

* cited by examiner

*Primary Examiner* — Susan Tran
(74) *Attorney, Agent, or Firm* — Assouline & Berlowe, P.A.; Loren Donald Pearson

(57) ABSTRACT

An antibacterial composition is formed from a polymer matrix that includes silver nanoparticles. The antibacterial composition can be used to provide surfaces that are to be touched. The antibacterial composition is particularly useful for forming cases for handheld electronic devices such as mobile telephones, smartphones, tablet computers, remote controls, and game controllers. A method of manufacturing items formed the composition can create materials with homogenously dispersed silver nanoparticles. Another process can be used to add antibacterial properties to existing surfaces.

9 Claims, No Drawings

ANTIBACTERIAL COMPOSITION, ANTIBACTERIAL CASES AND ACCESSORIES FOR HANDHELD ELECTRONICS, AND METHOD OF MAKING ANTIBACTERIAL CASES FOR HANDHELD ELECTRONICS

CROSS-REFERENCE TO RELATED APPLICATIONS

This application claims the benefit of U.S. Provisional Application No. 61/994,931, filed May 18, 2014, which is hereby incorporated by reference.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The invention relates to cases for handheld electronics with antibacterial properties, and more particularly, to cases made with materials containing silver-based nanoparticles.

Description of the Related Art

Cases can be added to handheld electronic devices for protection, ornamentation, personalization, and added utility (e.g. pockets, clips, and auxiliary batteries). Typically, the cases are made from a molded resin. In some instances, the polymer may be a thermoset in others a thermoplastic.

Polycarbonate is an example of a polymer used to make cases. Polycarbonate is a tough plastic used in a variety of goods, from bulletproof windows to CDs. It has enormous strength and is simultaneously lightweight and protective. Polycarbonate cases are often a bit bulky and typically do not provide the best aesthetics.

Polymers including carbon fibers are an alternative to polycarbonate. Carbon fiber can offer good protection depending on the cases design and thickness. While carbon fiber is durable, lightweight, and looks good, it is more expensive than other polymers.

Silicone is a third common material for cases. Silicon cases are useful for preventing scrapes, minor dings, and low impact drops. Silicone is an inexpensive material. Silicone cases are typically flexible. Silicone cases can add a good grip and a tacky feel to a handheld electronic device.

Thermoplastic polyurethane or TPU can be used to form cases. TPU provides a good grip and more shock protection and durability compared to silicon.

A *Wall Street Journal* article titled, "Calling all Germs" reported the problem of bacteria on mobile telephones. The article cited a study. A lab tested eight randomly selected phones from an office. The phones showed no signs of *E. coli* or staphylococci bacteria. But all phones showed abnormally high numbers of coliforms, a bacteria indicating fecal contamination. Of the eight phones tested by HML Labs of Muncie, Ind., there were between about 2,700 and 4,200 units of coliform bacteria. In drinking water, the limit is less than 1 unit per 100 ml of water.

The problem is exacerbated by manufactures of wireless devices voiding the device's warranty after the device has been cleaned with most antibacterial cleaners. APPLE®'s handheld device manual explicitly forbids the use of "window cleaners, household cleaners, aerosol sprays, solvents, alcohol, ammonia or abrasives." BLACKBERRY®'s advice is similar. Its manual states: "Do not use liquid, aerosol cleaners, or solvents on or near your BLACKBERRY® device."

To create antibacterial cases, additives have been incorporated in the polymer. Prior additives to wireless cases have been banned from the market or not satisfactory. Additives such as organic chlorine, quaternary ammonias, TRI-CLOSAN®, among others are bacteria-dynamic (antibacterial effect uncontrolled) and some others have already been banned from the market.

Handheld electronics include electronic devices that are to be operated with a hand of the user. Examples include mobile telephones, tablet computers, laptop computers, keyboards, telephones, pagers, game controllers, and remote controls.

Wiping an electronic device before use is not an acceptable solution. First, while microfiber cloths work great to remove oil and dirt, some bacteria remain. For some of the bacteria, you only need to ingest as few as ten (10) organisms to get sick. Second, the inconvenience of carrying a cleaning cloth and wiping down a device before each device is not acceptable to most users.

An example of a silver-containing nanoparticle dispersion is commercially available from TNS under the trade name NpAg_925. NpAg_925 is a dispersion based on silver nanoparticles and water. The dispersion is effective against bacteria (both gram-positive and gram-negative bacteria), as assessed against the standard antibacterial JIS Z 2801.

The production of nanoparticles is done through a chemical process inside reactors. A process called bottom top up where reducer and stabilizer agents are used to produce stable nanoparticles and monocomponents which create the product NpAg_925_SiO. To produce the powder compound the nanoparticles return to the reactor with ceramic powder in an order of 5 μm and food grade.

NpAg_925 is a colloidal dispersion of metallic silver in an aqueous medium, stabilized with organic molecules. The dispersion is a nonionic yellowish brown liquid that is soluble in water. The dispersion has a density of approximately 1.0 g/cm$^3$ at 25° C. The dispersion has a pH value of approximately 4.0. The solid content is about 1000 ppm.

The dispersion is compatible with additives and compounds based on water. The nanoparticles have an average size of 10 nm. The size range is 15-20 nm. The maximum wavelength is 400-410 nm.

NpAg_925 is a customized, monolithic antimicrobial product that can be applied in different segments. This is an aqueous emulsion containing silver nanoparticles stabilized with special organic molecules that ensure safe and effective application. The NpAg_925 product is nontoxic, easy to handle and to apply. The NpAg_925-SiO is an inorganic compound that functions as antibacterial developed with additives based on nanoparticles of metallic silver. It is classified as a bacteriostatic product designed to inhibit the formation and growth of pathogenic microorganisms.

The NpAg_925-SiO is suitable for incorporation into polymer matrices and ink formulations. During the application of the product it is necessary to ensure proper homogenization of the additive in the matrix in which it is added. Avoid contact with moisture and clumping of the granules so as to not result in problems of homogenization.

The quantity of NpAg_925-SiO to be added depends on the polymer matrix and the specific needs of each application.

The NpAg_925-SiO composition is made from the following components.

| COMPOSITION | CAS NUMBER | % BY WEIGHT |
|---|---|---|
| $H_2O$ | 7732-18-5 | 98.0-99.4% |
| Aminosilane | Confidential | 0.5-5.0 |
| Ag | 7440-22-4 | 0.1-2.0 |

Other compatible silver nanoparticles are available under the following trade names: Santaized and Microban.

BRIEF SUMMARY OF THE INVENTION

An object of the invention is to provide antibacterial cases and accessories for handheld electronics that overcome the disadvantages of the devices of this general type and of the prior art.

With the foregoing and other objects in view there is provided, in accordance with the invention, an antibacterial composition, an antibacterial case and accessory for handheld electronics, and a method of making antibacterial cases for handheld electronics.

An object of the invention is to provide a case made from material containing silver nanoparticles that combat pathogenic microorganisms. This technology prevents the product from local proliferation and transmission of bacteria, tested and approved under the standard "JIS Z 2801:2000."

Silver-containing nanoparticles can be mixed into the polymer matrix of cases for handheld electronics. The case can be a case that is used to contain and protect an existing handheld electronic device. The case can be the case that is integral with device. The case can be an auxiliary case that is added to improve and change the properties of the case. The auxiliary case can be supplied as an OEM part or sold aftermarket to supplement a primary case.

An object of the invention is to provide a case that can contact user's hands while preventing the case from becoming a source of proliferation and cross-contamination of pathogenic microorganisms, such as bacteria.

The product has silver nanoparticles that can combat pathogenic microorganisms. The technology adds silver nanoparticles to traditional cases during the manufacturing process to imbue the surface of the cases with anti-bacterial properties.

In accordance with the objects of the invention, a composition is provided. The composition can be used for form surfaces to be touched. The composition has antibacterial properties. The composition includes a polymer matrix and at least one part per million of silver-containing nanoparticles.

Silver containing nanoparticles are also known as silver nanoparticles. Silver nanoparticles are nanoparticles of silver, i.e. silver particles of between 1 nm and 100 nm in size. Silver nanoparticles include silver and silver oxide.

In accordance with the objects of the invention, an antibacterial case for a handheld electronic device is provided. The case includes a molded body shaped to receive a shape of the handheld electronic device. The molded body is composed of the composition described previously.

Examples of handheld electronic devices include mobile telephones, smartphones, remote controls, gaming controls, tablet computers, laptop computers, and personal music players. The case can be molded to have a shape that can receive a particular handheld electronic device.

By providing a case with antibacterial properties, the risk of infection created as the handheld electronic device is passed from user to user is reduced.

The antibacterial case can be an auxiliary, aftermarket, or accessory case that is sold separately from the handheld electronic device. The device is placed within the case to protect the device and to provide antibacterial qualities.

The case according to the invention can be the case or part of the case for the device as provided during manufacture. In other words, the case can be integrated as a part of the device.

The silver containing nanoparticles can be mixed homogenously in the resin. By being mixed throughout the resin, the resin can maintain its antibacterial properties even when the surface of the material is worn.

Depending on the desired performance characteristics of the case, the composition can be made from various polymers. The polymers can be a thermoplastic or a thermoset.

In accordance with the objects of the invention, a layer can be added to an existing case or electronic device. The layer includes silver nanoparticles that are deposited as a varnish. The varnish is then cured to bond the layer to the substrate's surface.

In accordance with the objects, the invention includes a method of making an antibacterial case for a handheld electronic device. The method includes providing a polymer matrix. The next step is heating the polymer matrix to make it melt. In the next step, at least one part per million of silver containing nanoparticles are admixed to create a silver nanoparticle polymer matrix. The next step involves injecting said silver nanoparticle polymer matrix into a mold to form a cast. The cast is shaped to receive the handheld electronic device.

Cases made according to the previous method have a homogenous dispersal of silver nanoparticles throughout the composition.

In accordance with the objects, the invention includes a further method of making an antibacterial case for a handheld electronic device. The method includes providing a varnish. The varnish is adherable to a material of a case when cured. The next step is admixing at least one part per million of silver containing nanoparticles into the varnish to create a silver nanoparticle varnish. The next step is coating a surface of the case with the silver nanoparticle varnish. The coated surface is to be handled during operational use of the handheld wireless electronic device. Next, the silver nanoparticle varnish is adhered to the surface of the case by curing the silver containing varnish.

A case made by the previously stated method has the advantage of having an antibacterial coating but at a lower price than a material that has silver nanoparticles dispersed throughout the entire case.

In accordance with the objects, the antibacterial composition can be used on any object that is formed from a resin. For example, the composition can be used to add antibacterial properties to a door handle or a clothing button (i.e. a fastener).

In the example of a door handle, an antibacterial door handle could be formed with a door handle, where the door handle has a surface that is to be held when operating a door.

A molded body is added to the door handle to cover at least a portion of the surface, and perhaps the entire surface. The molded body is formed from the previously described antibacterial composition.

An antibacterial button for fastening an item of clothing can be formed. The button includes a disc-shaped body. The disc-shaped body has two holes formed therein. The body is sized to fit through a button hole in an item of clothing. The body has a surface formed of the antibacterial composition. The entire body can be made of the antibacterial composition as well.

A particularly useful family of polymer matrixes is those that contain acrylonitrile butadiene styrene (ABS). To provide ABS with satisfactory antibacterial properties, the concentration of the silver containing nanoparticles should be at least two parts per million of the ABS polymer matrix.

Silver nanoparticles can be added to the mass of the product during manufacture.

Silver nanoparticles can be added to the surface.

The material forming the cases can be prepared by adding the additive powder or aqueous substance to the mass of the resin (throughout the product).

The material forming the cases can be prepared by adding the additive powder or aqueous substance during the pigmentation process, i.e. painting and other finishing processes.

A further object of the invention is to provide a case that has an anti-bacterial efficiency of 99.9%.

A further object of the invention is to provide an antibacterial additive that is effective enough at low concentrations that the cost of adding an effective amount is commercially feasible.

The silver-containing nanoparticles should be dispersible in an aqueous environment to allow the admixing of the nanoparticles in traditional productive processes.

Examples of silver-containing nanoparticles that can be used are available under the trade names NpAg_925, Sanitaized, and Microban To achieve the anti-bacterial properties, a concentrations of at least one part per million (≥1 ppm) of silver-containing nanoparticles is recommended. Tests indicate that concentrations beyond 100 ppm do not improve the antibacterial qualities of the resulting material.

To achieve satisfactory antibacterial properties in a handheld device, a minimum concentration of silver-containing nanoparticles is at least 2 pmm (0.025% of powder additive when applied to ABS). For solid additives, a recommended concentration between 0.025% (~2 ppm) and 0.60% (~50 ppm). For liquid additives, a recommended concentration is between 3 and 15 g/L (3 and 5 ppm).

Generally, the effective concentration of silver nanoparticles will depend on the particular polymer matrix. The concentration depends upon each polymer matrix, not on the product application. The activity occurs at concentrations as low as 2 ppm. For solid additives, the recommended concentration of silver nanoparticles between 2 ppm and 50 ppm. For liquid additives, the recommended concentration of silver nanoparticles is between 3 and 5 ppm.

The additive is embedded during the injection of the part. There is no change in the processing of the part.

In the case of varnish, the additive is incorporated into the varnish before the coating step.

Due to the low concentration of additive the cost for acquisition is less than the competitors. The additive does not interfere with other properties of the material, except coloring in some cases. The processing is also facilitated due to the low amount of additive used.

Other features that are considered as characteristic for the invention are set forth in the appended claims.

Although the invention is illustrated and described herein as embodied in antibacterial cases and accessories for handheld electronics, the invention should not be limited to the details shown in those embodiments because various modifications and structural changes may be made without departing from the spirit of the invention while remaining within the scope and range of equivalents of the claims.

The construction and method of operation of the invention and additional objects and advantages of the invention is best understood from the following description of specific embodiments when read in connection with the accompanying drawings.

BRIEF DESCRIPTION OF THE SEVERAL VIEWS OF THE DRAWING

Not Applicable

DETAILED DESCRIPTION OF THE INVENTION

Mobile telephone cases have been made from the following compositions

| EXAMPLE | Silver Nano Particles (PPM) | POLYMER MATRIX |
| --- | --- | --- |
| 1 | 1 | ABS |
| 2 | 2 | ABS |
| 3 | 50 | ABS |
| 4 | 100 | ABS |

The preferred type of silver nano particles are those sold under the trade name NpAG_925 by TNS Nanotecnologa Ltd.

A preferred method of creating the mobile telephone case includes the following steps. The polymer matrix is heated to melt the resin and to bring it to the normal processing condition of the material. As the resin is being pumped into a mold, the silver nanoparticles are mixed with the resin. The polymer matrix cools and sets within the mold. The material is removed.

What is claimed is:

1. An antibacterial case for a handheld electronic device, comprising:
   a molded body shaped to receive a shape of the handheld electronic device, said molded body being composed of a composition including a polymer matrix, and a at least one part per million of silver-containing nanoparticles, said silver-containing nanoparticles being disposed on micrometric silica, said micrometric silica being distributed throughout said polymer matrix, wherein said polymer matrix is a thermoplastic or a thermoset.

2. The antibacterial case according to claim 1, further comprising a handheld electronic device, said handheld electronic device being integrally enclosed by said molded body.

3. An antibacterial case for a handheld electronic device, comprising: a molded body shaped to receive a shape of the handheld electronic device, said molded body having an outer surface to be handled by a user when the handheld electronic device is being used; and
   a layer composed of a composition deposed on said molded body said composition including a polymer matrix, and a at least one part per million of silver-containing nanoparticles, said silver-containing nanoparticles being disposed on micrometric silica, said micrometric silica being distributed throughout said polymer matrix, wherein said polymer matrix is a thermoplastic or a thermoset.

4. A method of making an antibacterial case for a handheld electronic device, which comprises:
providing a polymer matrix;
melting said polymer matrix by heating said polymer matrix above a melting point of said polymer matrix;
admixing at least one part per million of silver-containing nanoparticles to create a silver nanoparticle polymer matrix, said silver-containing nanoparticles being disposed on micrometric silica, said micrometric silica being distributed throughout said polymer matrix, wherein said polymer matrix is a thermoplastic or a thermoset; and
injecting said silver nanoparticle polymer matrix into a mold to form a cast, said cast being shaped to receive the handheld electronic device.

5. A case for a handheld electronic device made according to the method described in claim 4.

6. A method of making an antibacterial case for a handheld electronic device, which comprises:
providing a varnish, said varnish being adherable to a material of a case when cured;
admixing at least one part per million of silver-containing nanoparticles into said varnish to create a silver nanoparticle varnish, said silver-containing nanoparticles being disposed on micrometric silica, said micrometric silica being distributed throughout said polymer matrix, wherein said polymer matrix is a thermoplastic or a thermoset;
coating a surface of the case to be handled during use of the handheld wireless electronic device with the silver nanoparticle varnish; and
adhering the silver nanoparticle varnish to the surface of the case by curing the silver containing varnish.

7. An antibacterial case made according to the method described in claim 6.

8. The antibacterial composition according to claim 1, wherein:
said polymer matrix includes acrylonitrile butadiene styrene; and
said silver containing nanoparticles form at least two parts per million of said polymer matrix.

9. The method according to claim 4, wherein:
said silver nanoparticles are disposed on micrometric silica; and
said silver containing nanoparticles form at least two parts per million of said polymer matrix.

* * * * *